(12) United States Patent
Grondin et al.

(10) Patent No.: US 10,729,390 B2
(45) Date of Patent: Aug. 4, 2020

(54) ROTARY COLLIMATOR FOR DETERMINING THE POSITION OF AN ELEMENT PROVIDED WITH SENSORS IN AN X-RAY IMAGING SYSTEM

(71) Applicants: SURGIQUAL INSTITUTE, La Tronche (FR); UNIVERSITÉ GRENOBLE ALPES, Saint Martin d'Hères (FR); CENTRE HOSPITALIER UNIVERSITAIRE DE GRENOBLE, La Tronche (FR)

(72) Inventors: Yannick Grondin, Arbin (FR); Philippe Augerat, St Ismier (FR); Philippe Cinquin, St Nazaire les Eymes (FR); Laurent Desbat, La Tronche (FR); Marion Decrouez, Chambery (FR)

(73) Assignees: SURGIQUAL INSTITUTE, Meylan (FR); UNIVERSITÉ GRENOBLE ALPES, Saint Martin d'Heres (FR); CENTRE HOSPITALIER UNIVERSITAIRE DE GRENOBLE, La Tronche (FR)

( * ) Notice: Subject to any disclaimer, the term of this patent is extended or adjusted under 35 U.S.C. 154(b) by 147 days.

(21) Appl. No.: 15/770,954

(22) PCT Filed: Oct. 25, 2016

(86) PCT No.: PCT/EP2016/075698
§ 371 (c)(1),
(2) Date: Apr. 25, 2018

(87) PCT Pub. No.: WO2017/072125
PCT Pub. Date: May 4, 2017

(65) Prior Publication Data
US 2018/0353146 A1    Dec. 13, 2018

(30) Foreign Application Priority Data

Oct. 26, 2015  (FR) ...................... 15 60194

(51) Int. Cl.
*A61B 6/06*        (2006.01)
*A61B 6/12*        (2006.01)
(Continued)

(52) U.S. Cl.
CPC .................. *A61B 6/12* (2013.01); *A61B 6/03* (2013.01); *A61B 6/06* (2013.01); *A61B 6/4266* (2013.01);
(Continued)

(58) Field of Classification Search
CPC .... A61B 6/00; A61B 6/06; A61B 6/12; A61B 6/4441; A61B 6/5205; A61B 6/547;
(Continued)

(56) References Cited

U.S. PATENT DOCUMENTS 5,923,727 A    7/1999   Navab
6,490,475 B1  12/2002   Seeley et al.
(Continued)

FOREIGN PATENT DOCUMENTS

FR    2 841 118 A1   12/2003
WO    0137287 A1      5/2001

OTHER PUBLICATIONS

International Search Report for International Application No. PCT/EP2016/075698 dated Jan. 24, 2017.
(Continued)

*Primary Examiner* — Jurie Yun
(74) *Attorney, Agent, or Firm* — Pearne & Gordon LLP

(57) ABSTRACT

The invention relates to an X-ray imaging device including a rotary collimator having a region (22) which is opaque to X-rays, a first slot (24) and a second slot (26), which are
(Continued)

transparent to X-rays and extend in two different directions, passing through the opaque region, the collimator making it possible to determine the position of an element provided with X-ray sensors in an imaging system (FIG. 1).

14 Claims, 8 Drawing Sheets

(51) Int. Cl.
*A61B 6/00* (2006.01)
*G01T 1/164* (2006.01)
*G01T 7/00* (2006.01)
*A61B 34/20* (2016.01)
*G21K 1/04* (2006.01)
*A61B 6/03* (2006.01)
*A61B 90/00* (2016.01)

(52) U.S. Cl.
CPC .......... *A61B 6/4441* (2013.01); *A61B 6/5205* (2013.01); *A61B 6/547* (2013.01); *A61B 6/585* (2013.01); *A61B 34/20* (2016.02); *G01T 1/1648* (2013.01); *G01T 7/00* (2013.01); *G21K 1/043* (2013.01); *A61B 6/4085* (2013.01); *A61B 6/4405* (2013.01); *A61B 2090/3764* (2016.02)

(58) Field of Classification Search
CPC ........... A61B 6/585; A61B 6/582; A61B 6/58; A61B 34/20; A61B 2090/3764; G01T 7/00; G01T 1/164; G01T 1/1648; G21K 1/04; G21K 1/043; G21K 1/02
USPC .......................... 378/147, 150, 151, 205, 207
See application file for complete search history.

(56) References Cited

U.S. PATENT DOCUMENTS

| 7,065,393 | B2 | 6/2006 | Sati et al. |
| 2008/0118023 | A1 | 5/2008 | Besson |
| 2017/0205360 | A1 | 7/2017 | Cinquin et al. |

OTHER PUBLICATIONS

Preliminary French Search Report for French Application No. 1560194 dated Jun. 24, 2016.
Xiao-Shan Gao, "Complete Solution Classification for the Perspective-Three-Point Problem". IEEE Transactions on Pattern Analysis and Machine Intelligence, vol. 25, No. 8, Aug. 2003.
Paul J. Besl, et al., "Method for Registration of 3D Shapes", IEEE Transactions on Pattern Analysis and Machine Intelligence, vol. 14, No. 2, Feb. 1992, IEEE.
Shahram Amiri et al.,"A Low-Cost Tracked C-arm (TC-arm) Upgrade System for Versatile Quantitative Intraoperative Imaging", Published online Dec. 10, 2013, DOI 10.1007/s11548-013-0957-9, Springer.

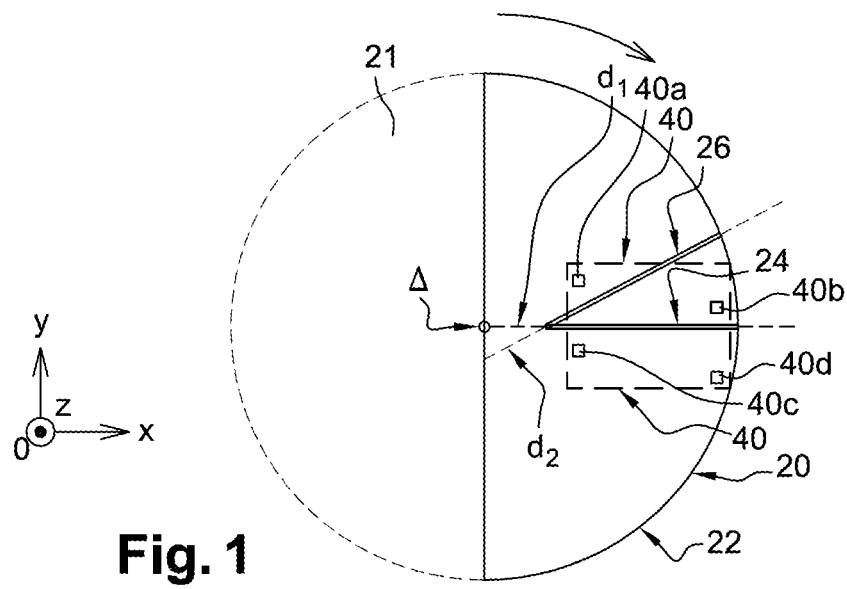
Fig. 1
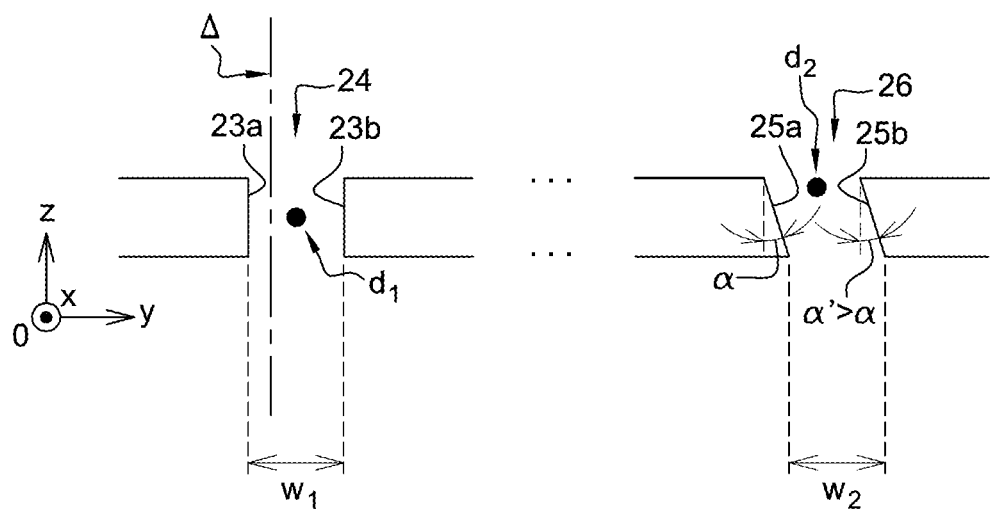
Fig. 2A     Fig. 2B

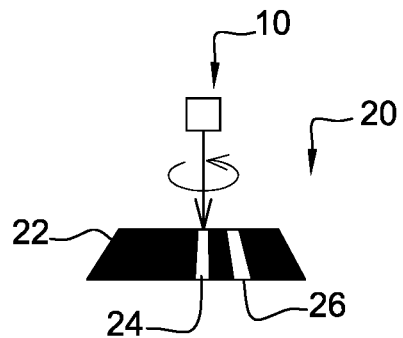
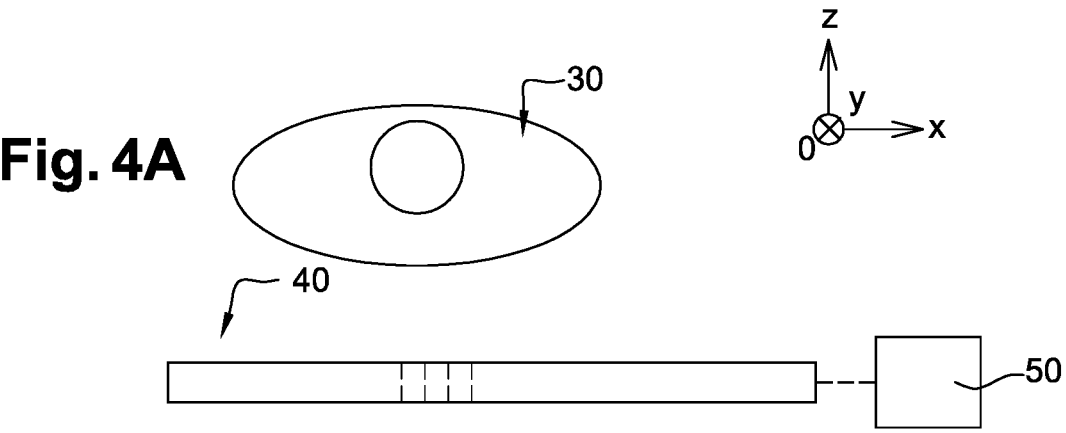
Fig. 4A
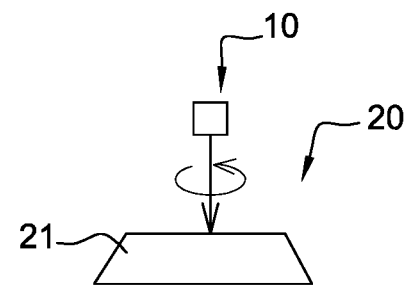
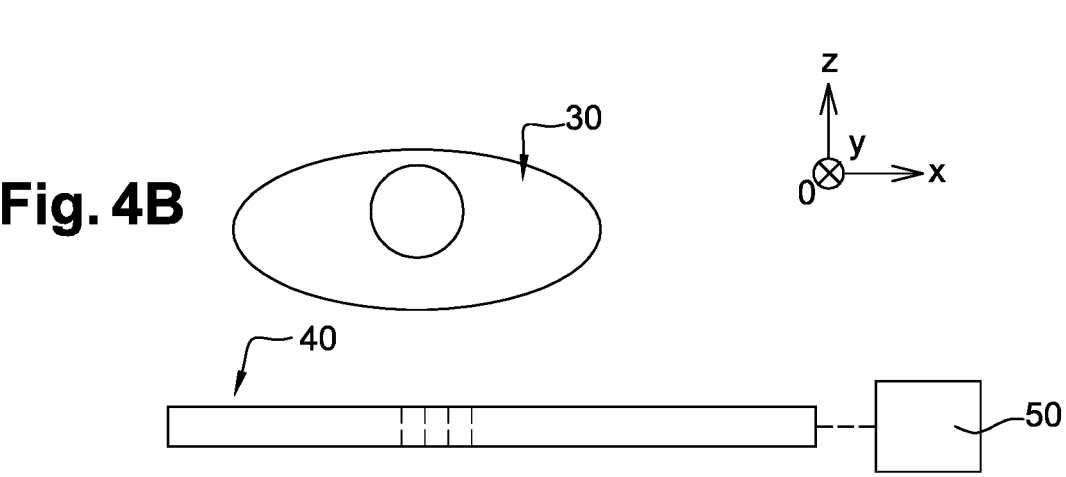
Fig. 4B

ROTARY COLLIMATOR FOR DETERMINING THE POSITION OF AN ELEMENT PROVIDED WITH SENSORS IN AN X-RAY IMAGING SYSTEM

TECHNICAL FIELD AND PRIOR ART

The present invention pertains to the field of X-ray imaging, and more specifically relates to that of the spatial localisation of elements in an X-ray imaging system.

It applies notably to so-called interventional imaging during which it is sought to determine precisely the positioning of a tool at the same time as an acquisition of images is carried out, for example during a surgical intervention or an operation carried out using this tool.

It also applies to the calibration of an X-ray imaging system, and makes it possible to determine the position of an imager with respect to a given coordinate system or to an X-ray source.

The document FR 2 841 118 describes an X-ray imaging system including a means for determining the positioning of a radiography apparatus by means of a sight fixed on an object of which an image is acquired.

In such a system the image of the sight interferes with that of the object that it is wished to study.

The document U.S. Pat. No. 6,490,475 describes for its part a fluoroscopy system in which the positioning of elements of the system is determined by means of markers. A digital processing is then carried out in order to be able then to remove the imprint of these markers from the final image.

The document U.S. Pat. No. 7,065,393 relates to a method for calibrating an X-ray imaging system by means of inertial sensors arranged on different elements of the system.

This type of sensor may be subjected to perturbations and pose problems of reliability.

The problem is posed of finding a novel device making it possible to determine in a reliable manner the position of an element provided with sensors in an X-ray imaging system.

DESCRIPTION OF THE INVENTION

According to one aspect, the present invention relates to an X-ray imaging system including a collimator formed of a support capable of being rotationally moveable around itself and with respect to an axis of rotation, the support including a region which is opaque to X-rays, at least one first slot and at least one second slot passing through said opaque region, the first slot and the second slot being transparent to X-rays, the first slot and the second slot each extending in a given plane parallel to the main plane of the support and respectively in a first direction passing through the axis of rotation and in a second direction which is not secant to the axis of rotation of the collimator.

By means of such a device it is possible to determine in a reliable manner the position in a given coordinate system of an element provided with X-ray sensors intended to receive X-ray beams coming from the slots of the collimator.

Such a collimator makes it possible to estimate in a precise manner the position of said element while limiting the dose of X-rays received.

Advantageously, the first slot and the second slot have different widths. This can enable a detection device to establish a distinction between an X-ray beam coming from the first slot and an X-ray beam coming from the second slot.

Another means of establishing such a distinction is to provide slots with different compositions. The first slot may then be constituted of a first radio-transparent material, whereas the second slot is constituted of a second radio-transparent material.

Advantageously, the support is further provided with a region transparent to X-rays situated in the given plane and juxtaposed with said region.

With such a layout of the collimator, it is possible to successively mask then expose an X-ray source in front of which said collimator is arranged and rotated, which makes it possible to alternate an imaging phase and a phase in which the collimator is used to determine a position of a detection element.

According to another aspect, one embodiment of the present invention provides an X-ray imaging system including:
  an X-ray source,
  a means for determining the position of at least one element with respect to a given coordinate system, the element being provided with one or more X-ray sensors, the determination means including:
  a device as defined above,
  a processing unit configured to determine at least one intersecting straight line between a first X-ray beam and a second X-ray beam detected by a same X-ray sensor among said sensors, the first beam coming from the X-ray source and having passed through the first slot and the second X-ray beam coming from the X-ray source and having passed through the second slot.

The imaging system is preferably provided with an imager.

When the support of the collimator is provided with a region which is radio-transparent to X-rays juxtaposed with the radio-opaque region, the system may be laid out such that, during a rotation of the collimator around itself, the source is during a first phase exposed to an imager through the transparent region then during a second phase masked partially from this imager by the opaque region and exposed solely through the first slot and the second slot.

In this case, the processing unit may be synchronised with the collimator in such a way that:
  during said first phase the processing unit triggers the acquisition of at least one radiographic image by the imager,
  during said second phase the processing unit estimates the position of said element.

It is thus possible to produce a radiographic image during the first phase and to realise a navigation of said element or a calibration of the imaging system during the second phase.

According to one possible embodiment, the element of which the position is determined is an imager provided with X-ray sensors, preferably at least 4 X-ray sensors.

These sensors may be pixels of the imager or specific sensors arranged on a matrix of pixels of the imager.

In this case, the determination means are configured in particular to determine the position of the imager with respect to the X-ray source.

According to another possible embodiment, the element of which the position is determined is an object that can be displaced with respect to the X-ray source, such as a surgical tool, to which the X-ray sensor or sensors is or are attached.

In this case, the X-ray imaging system may further include:
  an imager capable of producing a radiographic image and
  a display device for displaying a radiographic image produced by the imager and taking into account a displacement of the object.

According to one possible embodiment, the imaging system may be of C-arm type.

One embodiment provides a collimator that can be displaced with respect to the X-ray source outside of its axis of rotation. In this case, it is possible to provide a collimator with uniquely an opaque region passed through by radio-transparent slots. Once a position of the element has been detected, in order to make it possible to perform an image acquisition, the collimator may be displaced and removed from the path between the X-ray source and an imager.

According to another aspect, one embodiment of the present invention relates to a method for calibrating an X-ray imaging system as defined above and in which said element is an imager provided with at least 4 X-ray sensors. This method includes a determination of the position of the imager with respect to the source or with respect to a reference coordinate system linked to a room in which the imaging system is located, this determination of the position of the imager including an estimation by a processing unit coupled to the imager of at least 4 distinct straight lines each linking the source and one sensor among said at least 4 sensors of the imager.

BRIEF DESCRIPTION OF THE DRAWINGS

The present invention will be better understood on reading the description of exemplary embodiments given for purely indicating purposes and in no way limiting, and by referring to the appended drawings in which:

FIG. 1 illustrates an example of rotary collimator provided with a radio-opaque region passed through by radio-transparent slots, the collimator being intended to be integrated in an X-ray imaging system to make it possible to determine the position of an X-ray detector element within the system, FIGS. 2A-2B illustrate a particular example of layout of the radio-transparent slots in the thickness of the radio-opaque region of the collimator, FIGS. 4A-4B illustrate different positions of an X-ray imaging system provided with the rotary collimator and configured to carry out alternately a determination of the position of an X-ray detector and a production of a radiographic image of a target object.

Figure 3:
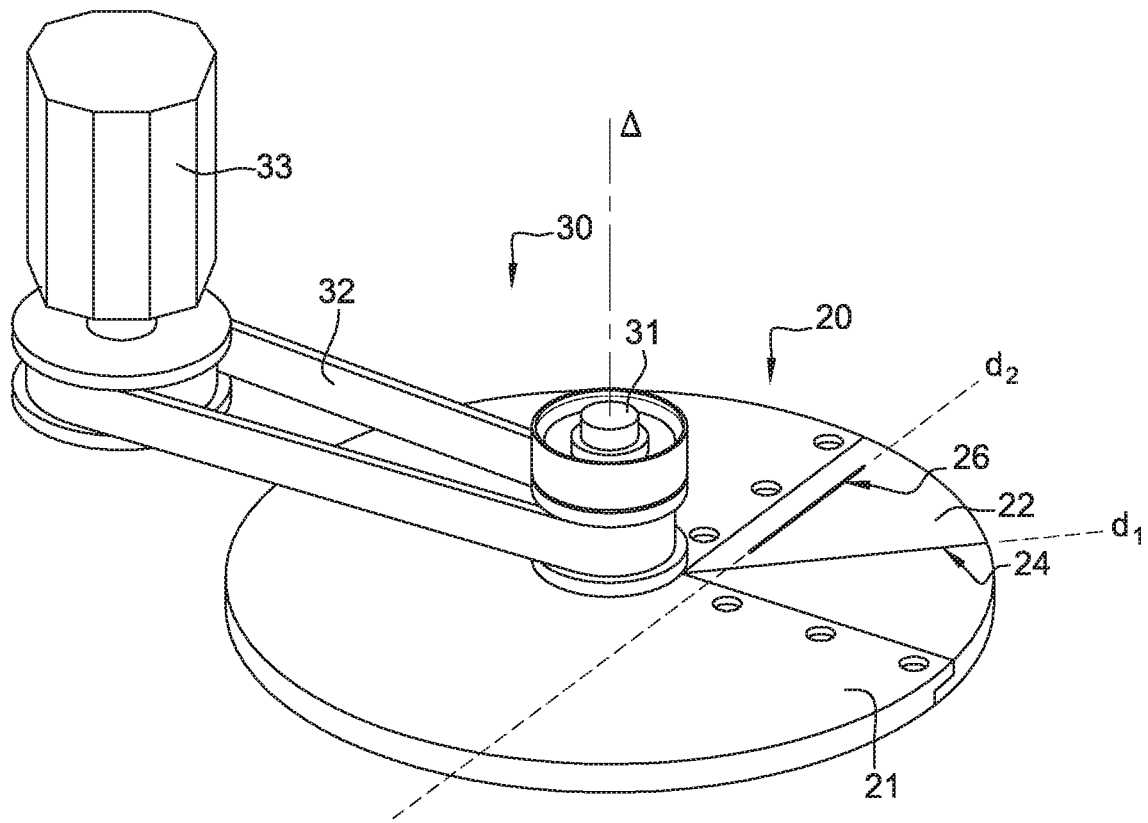
FIG. 3 illustrates an example of device for rotationally driving the collimator.

Identical, similar or equivalent parts of the different figures bear the same numerical references so as to make it easier to go from one figure to the next.

The different parts represented in the figures are not necessarily according to a uniform scale in order to make the figures more legible.

DETAILED DESCRIPTION OF PARTICULAR EMBODIMENTS

Reference is firstly made to FIG. 1 in which an example of rotating target also called collimator is represented.

The collimator is used to determine the positioning in a given coordinate system of at least one element capable of detecting X-rays. This element may be for example an X-ray detector 40 provided with sensors 40*a*, 40*b*, 40*c*, 40*d* situated in a same plane.

The collimator is here represented according to a top view and formed of a support 20 capable of being rotated around itself in front of an X-ray source. The X-ray source (not represented) is for example in the form of an X-ray emitting tube. The axis of rotation Δ of the support 20 passes through a normal to the main plane of the support 20 that is to say a plane which passes through the support 20 and which is parallel to the plane [O; x; y] given in FIG. 1. The collimator 20 is intended to be arranged at a predetermined and known distance from the X-ray source.

In this particular exemplary embodiment, the support 20 is a plate, for example in the form of a disc or a portion of disc, with a radio-opaque region 22 made of a material having a high absorption capacity vis-à-vis X-rays such as for example lead or tungsten. The plate may have a thickness (measured parallel to the z axis of a reference point [O; x; y; z] given in FIG. 1) of the order of several millimetres. The radio-opaque region 22 of the support 20 is passed through by two slots 24, 26 transparent to X-rays. The slots 24, 26 may be empty or filled with a material having a low absorption vis-à-vis X-rays, such as for example carbon. The slots 24, 26 have a width (measured in the plane [O; x; y] of the reference point [O; x; y; z]) which may be for example less than 1 mm.

The two radio-transparent slots 24, 26 are laid out on the support 20 in such a way that in a plane parallel to the main plane of the support 20, a first slot 24 extends in a first direction $d_1$ which is secant to the axis of rotation Δ of the support 20, whereas a second slot 26 extends for its part in a second direction $d_2$ which does not pass through the axis of rotation Δ of the support 20. In this particular exemplary embodiment, the directions $d_1$ and $d_2$ of the slots 24, 26 are not collinear and form a non-zero angle with respect to each other.

With such a layout of the collimator, when the support 20 is rotating around itself with respect to the axis of rotation Δ, it is possible for an X-ray sensor to detect a first X-ray beam coming from the first slot 24 and a second X-ray beam coming from the second slot 26.

A difference in width between the slots 24, 26 may be provided in order to establish a distinction between the first beam and the second beam, the width (dimension measured parallel to the plane [O; x; y] of the slots) having an influence on the time width of signals received by the sensors 40*a*, 40*b*, 40*c*, 40*d*.

Thus, when the second slot 26 is provided for example with a width $W_2$ greater than that $W_1$ of the first slot, due to the fact of the reception of a beam having passed through the first slot, a first signal is captured of smaller time width than a second signal induced by a second beam having passed through the second slot, the first and the second signal having substantially equal amplitudes.

Another means for establishing a distinction between a first beam coming from the first slot and a second beam coming from the second slot is to provide them with different compositions. For example, the first slot 24 in the form of a hole is thereby constituted of air whereas the second slot is filled with a radio-transparent material for example a plastic material of a predetermined thickness. The amplitude of a signal having passed through the first slot and detected by the sensor may be different to that of the slot uniquely constituted of air if a sufficient thickness of plastic material is considered.

In order to take account of the divergence of the X-ray beam coming from the X-ray source, the first slot 24, and the second slot 26 may be provided with different transversal sections. "Transversal" section is taken to mean a section taken in a plane orthogonal to the main plane of the support 20, in other words in a plane that is parallel to the vector z of the reference coordinate system [O; x; y; z] in FIG. 1.

Transversal sectional views of the first slot 24 and the second slot 26 are given respectively in FIGS. 2A and 2B.

The first slot 24, i.e. that situated on a radius of the disc and which cuts the axis of rotation Δ has a transversal section delimited between a zone 23a of the radio-opaque region 22 which is parallel to a normal to the main plane of the support 22 and to the axis of rotation Δ and another zone 23b. The transversal section may be rectangular. In this case the other zone 23b is parallel to a normal to the main plane of the support 22. In order to take account of the divergence of the X-ray beam, the other zone 23b may in an alternative form a non-zero angle with the normal to the main plane of the support 22.

The second slot 26, i.e. that which is not situated on a radius of the disc and which does not cut the axis of rotation Δ has a defined transversal section between the zones 25a, 25b which are inclined and form respectively an angle α and an angle α' (with α'>α>0) with respect to the main plane of the support 20 or to the axis of rotation Δ. The inclination of the zones 25a, 25b is provided as a function of the divergence of the X-ray beam emanating from the X-ray source.

The slots 24, 26 scan substantially the same spatial field. In order that the whole of the surface of the detector 40 is scanned by X-rays coming from the source 10 and passing through the slots 24, 26, it is possible to provide slots of length for example greater than 4 cm, in the case for example where a detector 40 is considered of maximum dimension of 40 cm and an enlargement factor of the X-ray beam of the order of 10 between the collimator 20 and the detector 40.

The X-ray source/collimator system makes it possible to produce two rotating X-ray beams, each beam passing through a slot 24 or 26 which can be assimilated with an X-ray plane. The source-collimator system thus makes it possible to generate two rotating X-ray planes which the X-ray sensors of the detector 40 are capable of detecting.

The detection of these planes by a given X-ray sensor of the detector 40 makes it possible to deduce an intersecting straight line between these two planes linking a sensor to the X-ray source. If for example 4 different sensors 40a, 40b, 40c, 40d of the detector 40 are considered it is possible to provide a detection of 4 different intersecting straight lines. By detection of secant X-ray planes it is possible to determine the position of the X-ray detector 40, in particular with respect to the source 10.

One embodiment of the invention thereby provides a means for determining the position of the detector 40 by detection of secant X-ray beams or planes coming from the collimator.

The positioning of the slots 24, 26 on the support 20 and in particular the position and the orientation of the first slot 24 with respect to the second slot 26 is known from this determination means, as well as the speed of rotation of the support 20.

Thus, the positioning of one with respect to the other of the two X-ray beams or planes passing through the slots 24, 26 is known. The time interval between an instant where an X-ray sensor is covered by the first X-ray beam or plane passing through the first slot and an instant where this same X-ray sensor is covered by the second beam or X-ray plane passing through the first slot is also known since it depends on the speed of rotation of the support 20.

The rotation of the support 20 of the collimator is for its part ensured by a drive device of which an exemplary embodiment is given schematically in FIG. 3. In this particular example, the support is in the form of a disc linked at its centre to a shaft 31 rotationally driven by means of a belt 32 itself connected to another shaft 33.

One particular embodiment provides a removable collimator and/or one which may be displaced within the imaging system. Thus, a device (not represented) making it possible to displace the collimator 20 with respect to the source 10 and to remove it from the field of vision of the detector 40 may be provided.

Advantageously, the support 20 of the collimator includes a region which is transparent to X-rays, either in the form of an empty portion around the opaque region 22 of the support 20 or in the form of a region of the support 20 made of radio-transparent material which is co-planar with the radio-opaque region 22.

In FIGS. 4A-4B is represented a radiological image acquisition system provided with a collimator as described previously.

The layout of the collimator with an opaque region 22 and a transparent region 21 enables, when it is rotated around itself, to alternate a first so-called localisation or calibration phase, during which the position is determined of an X-ray detector element, for example the detector 40 and a second image acquisition phase during which a radiological image of a target object 30 is generated. The imaging system may be applied to medical imaging, the considered target object 30 being in this case a patient.

In FIG. 4A, the collimator is located in a position corresponding to the localisation phase, the detector 40 seen from the source 40 being masked by the radio-opaque region 22 of the collimator. The dimensions of the collimator as well as its position with respect to the source 10 and to the detector 40 are provided in such a way that during the localisation phase, the X-ray beam coming from the source 10 and masked by the radio-opaque region 22 is only capable of reaching the detector 40 through the slots 24, 26.

The detector 40 is in this example in the form of an imager or a matrix of X-ray sensors spread out on a same plane. The detection of X-ray planes coming from the slots of the collimator may be carried out either by sensors integrated in the pixels of the matrix or the imager, or by specific sensors arranged on the matrix of pixels. An example of X-ray sensor includes a scintillator of CsI crystal type converting X-rays into UV or visible light, the crystal being arranged on a light sensitive TFT (Thin Film Transistor). Another example of sensor integrates a semiconductor material, such as amorphous selenium, capable of directly converting X-rays into electrical charges. The X-ray sensors used may have for example a square shape with sides for example of the order of 1 mm. The sensors used have preferably a time response less than 0.1 ms.

In FIG. 4B, the collimator is located in a position corresponding to the image acquisition phase, the detector 40 seen from the source 40 being visible through the radio-transparent region 21 of the collimator. The layout of the collimator is such that during the image acquisition phase, the X-ray beam coming from the source 10 passes through the radio-transparent region 21. In this case, no radio-opaque zone of the collimator perturbs the radiological image of the target object 30.

Thus, for a same turn of the collimator around itself the duration of which may be for example of the order of 200 ms, one passes successively from a localisation phase to an image acquisition phase and it is thereby possible to successively determine the position of the detector 40 while limiting irradiation, then to produce a radiographic image without perturbing or congesting the field of vision of the imager.

To make it possible to determine the position of the detector 40 in a given reference coordinate system, for example with respect to the X-ray source or a given fixed point, by means of a detection of X-ray planes coming from the slots 24, 26 of the collimator, the detector 40 may be coupled to a processing unit 50 integrated or connected to the detector.

The digital processing unit 50 may be provided with at least one processor, at least one memory module and at least one input peripheral. The processor may be integrated in the detector 40 and for example be in the form of a microprocessor, or a FPGA circuit or instead be connected to the detector 40 and for example in the form of a processor of a central unit or work station. A network of processors may also be implemented. The memory module may include, for example, a read only memory ROM, an erasable programmable read only memory EPROM, a dynamic random access memory DRAM or any other type of volatile and/or non-volatile memory. Algorithms in the form of instructions may be stored in the programme memory, and make it possible to carry out digital processing steps notably to determine the position of the detector 40 from signals coming from X-ray sensors and producing images of the target object 30. A programme, making it possible to implement such processing operations, may be saved in the memory module of the processing unit 50 or any memory support that can be read by the processing unit 50.

The processing unit 50 is also configured to make it possible to synchronise the radiological image acquisition and localisation phases with the rotation of the collimator. In particular, the image acquisition phase, during which an image is produced is implemented in a time interval during which the radio-transparent region exposes the source 10 to the detector 40. The localisation phase, during which an estimation of the position of an X-ray detector element is carried out, is conducted in a time interval during which the radio-opaque region partially masks the source 10 from the detector 40, this only being visible through the slots 24, 26. To perform such a synchronisation, the processing unit 50 has available information relative to the speed of rotation of the collimator.

The localisation phase makes it possible to determine the position of the detector 40.

An example of method for determining the position of the detector 40 with respect to a given coordinate system, for example with respect to the source 10, will now be described in relation with FIGS. 5 and 6.

Figure 5:
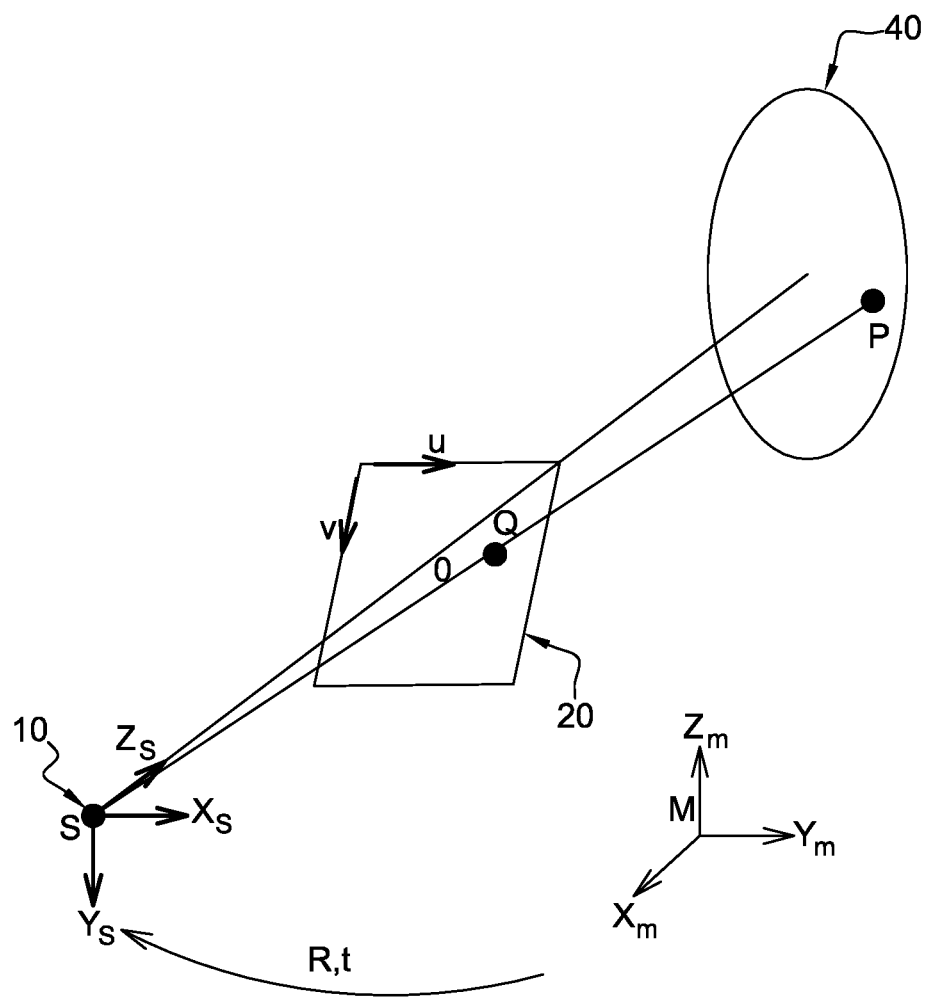
FIG. 5 illustrates in a schematic manner a modelling of a source-collimator-detector system.

Reference is now made to FIG. 5 in which the source-collimator-detector system is represented schematically.

To carry out a modelling of this system, the processing unit 50 may use different frames of references, of which one coordinate system called world coordinate system of which the centre is a point M and in which the coordinates of a point P are expressed for example in metres.

A source coordinate system of which the centre S is the X-ray source 10 is also defined. The source coordinate system is provided with a first axis Xs parallel to a vector u, a second axis YS parallel to another vector v. A third axis of the source coordinate system is for its part normal to the plane (u, v) defined by the vectors u and v.

This plane (u, v) also called "image plane" or "collimator plane" here corresponds to the main plane of the support 20 of the collimator in which are located the slots 24, 26. A coordinate system is here considered corresponding to the plane of the collimator 20. This coordinate system makes it possible to express the coordinates of the elements of interest of the projective system.

The coordinates of a point P in the source coordinate system may be expressed for example in metres.

A point O called the "main point" corresponds to an orthogonal projection of the centre S on the plane of the support 20 of the collimator. The distance SO is noted f and is called "focal distance". O has for coordinates (u0, v0) in the image coordinate system, the straight line SO is called "main axis".

The projection of a point P of the detector 40 on the collimator plane (u, v) at the point Q is expressed by a combination of geometric transformations:

The coordinates of the point P are expressed in the world coordinate system (M, Xm, Ym, Zm) and are converted into the coordinate system of the source (S, Xs, Ys, Zs): they are extrinsic parameters. P is next projected on the plane (u, v) of the collimator at the point Q as a function of the internal characteristics of the source-detector system: they are intrinsic parameters.

Let us note the coordinates of P
In the world coordinate system: (X, Y, Z)
In the source coordinate system: (Xs, Ys, Zs)
This gives the relation:

$$\begin{bmatrix} X_s \\ Y_s \\ Z_s \end{bmatrix} = R \begin{bmatrix} X \\ Y \\ Z \end{bmatrix} + t = [R \mid t] \begin{bmatrix} X \\ Y \\ Z \end{bmatrix}$$

R, t are respectively an operation of rotation and translation which make it possible to pass from the world coordinate system to the source coordinate system. The operation of rotation R may be expressed as the product of 3 matrices of rotations, each of its 3 matrices representing a rotation around a given axis of the coordinate system.

Q is the projection of P in the plane of the collimator and has for coordinates (x, y, z) in the source coordinate system:

$$\begin{bmatrix} x \\ y \\ z \end{bmatrix} = \begin{bmatrix} f/Z_s & 0 & 0 \\ 0 & f/Z_s & 0 \\ 0 & 0 & f/Z_s \end{bmatrix} \begin{bmatrix} X_s \\ Y_s \\ Z_s \end{bmatrix}$$

This expression is obtained by the Thales' relationship. Q has for coordinates (u, v) in the plane of the collimator and this gives the relationship:

$$\begin{bmatrix} u \\ v \end{bmatrix} = \begin{bmatrix} k_u & 0 & u_0 \\ 0 & k_v & v_0 \end{bmatrix} \begin{bmatrix} x \\ y \\ 1 \end{bmatrix}$$

ku and kv are commonly metre into pixel conversion factors expressed in pixel/m. In our case, one remains in a metric system whether it is in the plane of the detector 40 or the plane of the collimator 20, thus giving ku=kv=k=1.

Consequently, the following relationship obtained between Q (u, v) and P(Xs, Ys, Zs):

$$\begin{bmatrix} au \\ av \\ a \end{bmatrix} = \begin{bmatrix} f & 0 & u_0 \\ 0 & f & v_0 \\ 0 & 0 & 1 \end{bmatrix} \begin{bmatrix} X_s \\ Y_s \\ Z_s \end{bmatrix} = K \begin{bmatrix} X_s \\ Y_s \\ Z_s \end{bmatrix}$$

K is a matrix representing the intrinsic parameters of the source-detector system: f, u0 and v0. f is the distance separating the source and the collimator 20 which is known from the processing unit 50, u0 and v0 being the Cartesian coordinates (in metres) of the main point in the plane of the collimator 20.

The relationship between a point P expressed in the world coordinate system and its projection Q in the plane (u, v) is:

$$Q = K[R|t]P$$

A calibration of an imaging system as described previously may be carried out in the factory, such that when said system is next used, the processing unit 50 knows at least one calibrated position, called "reference position" of the detector 40 relative to the source 10. Thus, respective reference positions of several X-ray sensors 40a, 40b, 40c, 40d of the detector 40 with respect to the source 10 are known. The position of the collimator 20 relative to the source 10 is also known from the processing unit 50.

When the imaging system is in operation, the detector 40 plane is no longer necessarily in its reference position and may be located in a new position that it is wished to determine. The position of the detector 40 with respect to the source 10 may be intended to vary, even while it is sought to obtain images of the target object 30.

Figure 6:
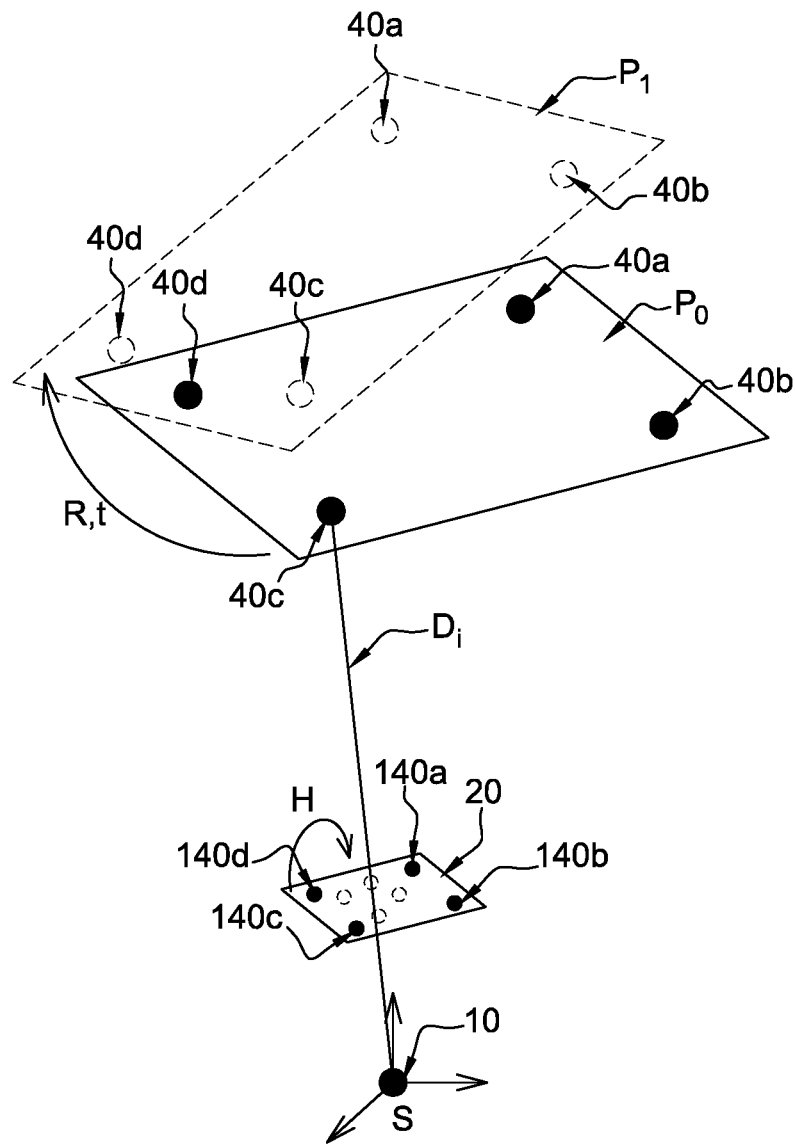
FIG. 6 illustrates in a schematic manner a first method for estimating the displacement of an imager in an imaging system provided with a rotary collimator.
Figure 7:
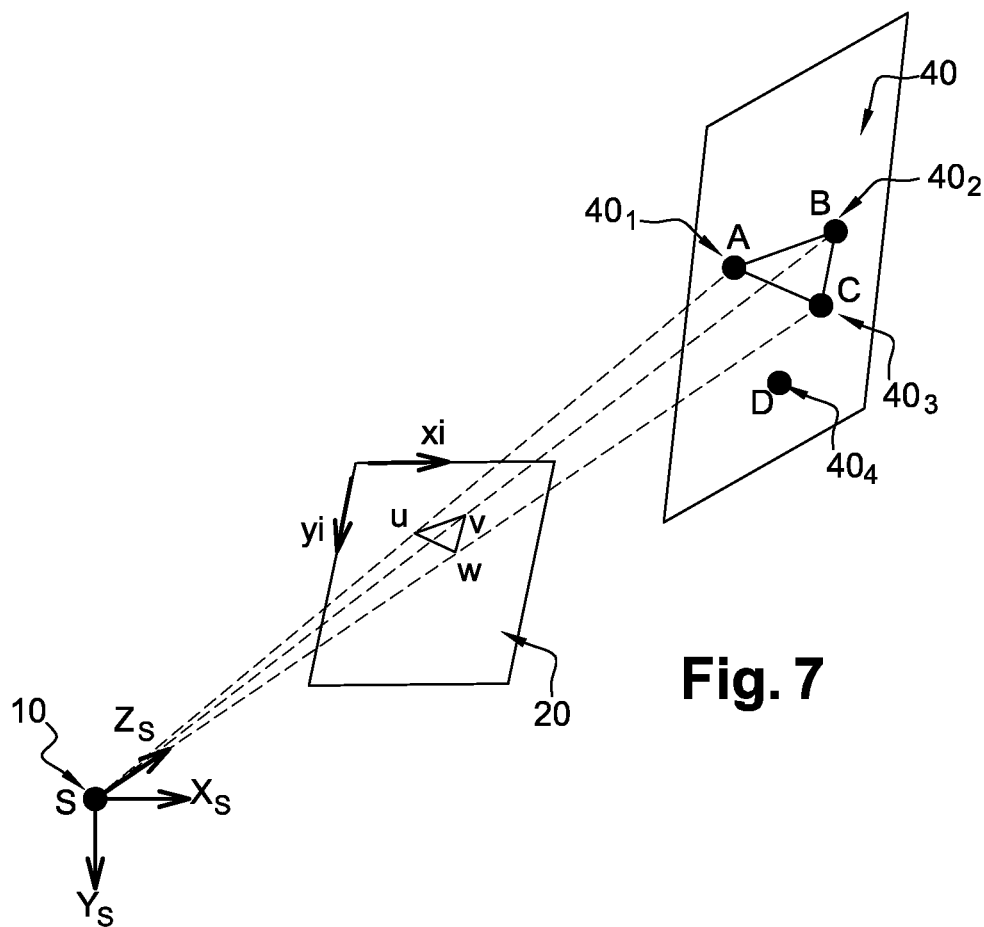
FIG. 7 illustrates in a schematic manner a second method for estimating the displacement of an imager in an imaging system provided with a rotary collimator.

A movement of the detector 40, and of some of its X-ray sensors 40a, 40b, 40c, 40d from a position $P_0$, for example the reference position to a new position $P_1$ is represented schematically in FIG. 6.

Generally speaking, each new position of the detector 40 and thus of a sensor of the latter is the result of a rotation R with respect to the coordinate system linked to the source 10 and a translation t of the reference position.

The processing unit 50 is configured to estimate these operators R, t in order to determine each new position of the detector plane 40.

To determine a new position $P_1$ of the detector 40, the processing unit 50 is configured to calculate a homography H making it possible to pass from respective projections 140a, 140b, 140c, 140d of the sensors 40a, 40b, 40c, 40d given on the plane of the collimator 20 when the detector 40 is located in a first position $P_0$ to the respective projections 140a, 140b, 140c, 140d of the sensors 40a, 40b, 40c, 40d given on the plane of the collimator 20 when the detector 40 is located in this new position $P_1$.

A projection of a sensor of the detector 40 in the plane of the collimator 20 corresponds to the intersection of a straight line linking the source 10 and said sensor with the main plane of the support 20, said straight line being itself the intersection of two X-ray planes coming from the slots 24, 26 of the collimator.

To perform the calculation of the homography H, the processing unit 50 carries out a matching of the projections of the X-ray sensors 40a, 40b, 40c, 40d on two series of measurements.

This matching may be carried out on the basis of the hypothesis that the displacement of the detector 40 plane is small, in particular less than several mm or degrees. Thus, a proximity criterion of the projections is used to carry out the matchings.

Thus, when it is sought to match a projection with another projection, it is the closest projection that is considered.

The sensors 40a, 40b, 40c, 40c of the detector 40 used to determine the position of the detector 40 are preferably distant from each other in order to avoid any matching error. For example, when a detector of rectangular shape is considered, the sensors 40a, 40b, 40c, 40c are spread out preferably near to each summit of the rectangle formed by the detector.

It is possible to start from the hypothesis that the matrix of intrinsic parameters K is unchanged in the two positions of the detector 40 plane in so far as the collimator 20 is integral with the source 10 or when the source collimator 20 distance is fixed.

A relationship then exists linking all the operators and the matrix of intrinsic parameters K:

$$HK = K(R - t\vec{n}/d)$$

With $\vec{n}$ the normal of the detector 40 in the reference position $P_0$, and d, its distance with respect to the source coordinate system. The matrix K is known and the homography H is calculated.

HK may be broken down into 3 matrices: the matrix K, the matrix of rotation R with respect to the coordinate system linked to S, and a matrix representing the product t $\vec{n}/d$, from which it is deduced.

In order that this method guarantees that the matrix of rotation R and the matrix of translation t are obtained in a univocal manner, preferably at least 4 X-ray sensors of the detector 40 or arranged on the detector 40 are used. In order to improve the precision and the rapidity of determining the position of the detector 40, it is possible to use measurements coming from a number of sensors greater than 4.

In an alternative of the method described previously, the determination of the position of the detector 40 with respect to a given coordinate system and in particular with respect to the source 10 may be carried out by means of a so-called P3P type method derived from methods described in the documents "Complete solution classification for the perspective-three-point problem", of Gao et al. (2003), IEEE Transactions on Pattern Analysis and Machine Intelligence, 25(8), 930-943 and "Method for registration of 3D shapes", of Besl et al. (1992), In Robotics-DL tentative pp. 586-606, International Society for Optics and Photonics.

A coordinate system (Xs, Ys, Zs) is considered of which the centre S is the X-ray source 10, a plane (xi, yi) of the collimator 20, points U, V, W, situated in the plane of the collimator 20 having for projections respectively the points A, B, C in the plane of the detector 40, and which correspond respectively to the locations of sensors $40_1$, $40_2$ and $40_3$, on the detector 40. The point D in the plane of the detector corresponding to another X-ray sensor $40_4$ is also considered. The angles $\varphi_{u,w}$, $\varphi_{v,w}$, $\varphi_{u,v}$ are moreover considered corresponding respectively to $\widehat{sUW}$, $\widehat{sVW}$, $\widehat{sUV}$.

The detector 40 is a planar device of which it is wished to determine the position and the orientation, by evaluating the distances SA, SB, SC, SD.

Thus, at least 4 points A, B, C and D, and thus at least 4 X-ray sensors $40_1$, $40_2$, $40_3$, $40_4$ are used here. As for the other method described previously in relation with FIG. 6, a number of sensors greater than 4 may be provided to improve the precision of the estimation of the position of the detector 40.

The sensors $40_1$, $40_2$, $40_3$, $40_4$ corresponding to the points A, B, C, D are each situated on an intersecting straight line between two X-ray planes having passed through the two slots of the collimator and having detected a signal corresponding to this intersection.

The calculations then implemented by the processing unit 50 are based on the following Al-Kashi formula: $AB^2 = SB^2 + SA^2 - 2SASB \cos \varphi_{u,v}$. For the 3 points A, B and C, non-collinear, this gives:

$$SB^2 + SC^2 - 2SBSC \cos \varphi_{v,w} - BC^2 = 0$$

$$SA^2 + SC^2 - 2SASC \cos \varphi_{u,w} - AC^2 = 0$$

$$SA^2 + SB^2 - 2SASB \cos \varphi_{u,v} - AB^2 = 0$$

If one divides by $SC^2$ and if one notes $y = SB/SC$ and $x = SA/SC$, this equation system is written:

$$y^2 + 1 - 2y \cos \varphi_{v,w} - BC^2/SC^2 = 0$$

$$x^2 + 1 - 2x \cos \varphi_{u,w} - AC^2/SC^2 = 0$$

$$x^2 + y^2 - 2xy \cos \varphi_{u,v} - AB^2/SC^2 = 0$$

If one notes $m = AB^2/SC^2$ and $am = BC^2/SC^2$ and $bm = AC^2/SC^2$, the following system is obtained:

$$y^2 + 1 - 2y \cos \varphi_{v,w} - am = 0$$

$$x^2 + 1 - 2x \cos \varphi_{u,w} - bm = 0$$

$$x^2 + y^2 - 2xy \cos \varphi_{u,v} - m = 0$$

$m = x^2 + y^2 - 2xy \cos \varphi u$ is replaced, in the two first equations, which gives the system:

$$(1-a)y^2 - ax^2 - (2 \cos \varphi_{v,w})y + (2a \cos \varphi_{u,v})xy + 1 = 0$$

$$(1-b)x^2 - by^2 - (2 \cos \varphi_{u,w})x + (2a \cos \varphi_{u,v})xy + 1 = 0$$

The positions of the sensors $40_1$, $40_2$, $40_3$, $40_4$, with respect to each other on the detector 40 are known, which in other words makes it possible to know AB, BC, AC.

The position of the collimator 20 with respect to the source 10 is known, which makes it possible to know SU, SV, SW as well as the angles $\varphi_u$, $\varphi_{u,w}$, $\varphi_{v,w}$.

By resolving the above system of equations 4 possible solutions of distances SA, SB, SC and 4 possible values of the vectors SA, SB and SC expressed in the coordinate system linked to the source may be deduced by the processing unit 50. The point D corresponding to the $4^{th}$ X-ray sensor $40_4$ in the plane of the collimator 20, enables the processing unit 50 to determine without ambiguity the position and the real orientation of the detector 40.

A localisation of the detector 40 with a localisation precision less than the dimension of sensor may be obtained by means of one or the other of the methods described previously.

Figure 8:
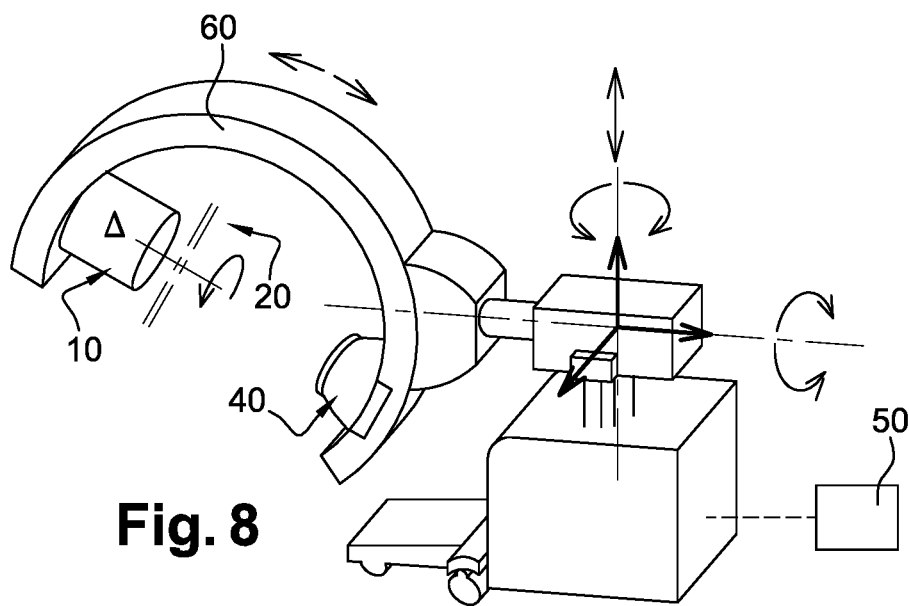
FIG. 8 illustrates a C-arm imaging system in which a rotary collimator is integrated.

According to a particular application example, a rotary collimator such as described previously may be integrated in an X-ray imaging system of C-arm type such as that represented for example in FIG. 8 in which the X-ray source 10 is connected to an X-ray detector 40 through an arched or C-shaped arm 60.

The source 10 and the detector 40 are intended to be displaced, and in particular to rotate around a target object, here a patient, to carry out projections according to several viewing angles. These projections are next exploited by the processing unit 50 coupled to the detector 40. The processing unit 50 is in this case further configured to implement a reconstruction algorithm in order to obtain a 3D or volumic image, representing several sections of the imaged target object. In this type of system employed for example in operating theatres, relative positioning information of the source 10 and the detector 40 may be used in order to construct 3D tomographic images.

Indeed, the input data of the reconstruction algorithm used by the image processing unit 50 to produce 3D images include the position of the C-arm device relative to the imaged object as well as the relative position of the source 10 and the detector 40. Yet potential mechanical imperfections as well as the effect of gravity can have a tendency to modify the distance between the source 10 and the detector 40. The processing unit 50 may be configured in such a way as to perform a succession of estimations of the position of the detector 40 in order to produce radiographic images, in particular dynamic images, of enhanced precision. These estimations can make it possible to perform a calibration of the imaging system in real time while it is in operation and while radiographic images are produced. This type of calibration, also called "on-line" calibration, may be carried for example during a surgical operation.

When the imaging system described previously is used to carry out tomography, in particular of CBCT (Cone Beam Computed Tomography) type, each image produced by the imager may be associated with intrinsic calibration parameters including detector positioning information and which is used by image reconstruction algorithms in order to produce an artefact-free image.

Apart from this type of so-called "intrinsic" calibration, the collimator device can make it possible to perform an "extrinsic" calibration.

Extrinsic calibration consists in determining the positions of the imaging system in a reference coordinate system linked to the place where the imaging system and the target object are located, for example a coordinate system linked to an operating theatre in which a patient is located in the case of an application to medical imaging during surgery.

Such a calibration is used to carry out a reconstruction of tomographic images (3D), to carry out a navigation of a surgical tool, or an image resetting, for example with tomodensitometric images (scanner) acquired earlier.

Extrinsic calibration includes an estimation of the position of the detector relative to the source by a method such as described previously, as well as a determination of the position of the source 10 in the reference coordinate system. The position of the source 10 may be determined by a localisation device known to those skilled in the art, for example an optical device such as described in the document US 5°923°727, or by an inertial measurement unit as described in the document: "A low-cost tracked C-arm (TC-arm) upgrade system for versatile quantitative intraoperative imaging", of Amiri et al., (2013). International Journal of Computer Assisted Radiology and Surgery, 1-17).

For a static C-arm imaging system, which can be used for example to perform a coronarography, in which the source 10 and the detector 40 are not moveable, another type of so-called "off-line" calibration may be implemented.

During this type of calibration, the relative positions of the X-ray source, and the detector 40 are determined by means of a collimator device as described previously before using the system to produce radiographic images.

An alternative embodiment of the collimator described previously provides a support with a surface this time entirely radio-opaque and passed through by two radio-transparent slots.

In this case, the collimator is used mainly to implement a localisation phase during which the position of one or more X-ray sensors or an X-ray detector is estimated, while detecting the intersection of the X-ray planes coming from the slots. During this localisation phase, the collimator 20 is thereby placed in the path of X-rays coming from the X-ray source 10.

Then, when this localisation phase is finished, and for example when a calibration of the imaging system has been carried out, the collimator may be next displaced with respect to the X-ray source in such a way that it is no longer located on its axis of rotation and in the path of X-rays between the source and the imager. It is then possible to perform an acquisition of a radiological image of a target object or of a patient by the imager without the collimator hindering this acquisition.

The passage from a localisation or calibration position to a position of acquisition of the imaging system by displacement of the collimator is ensured by a displacement device.

With such a layout of the collimator, the dose that a patient is likely to receive during a localisation or calibration phase is very low and for example 100 times less than the dose to which he or she may be exposed during an image acquisition phase carried out without collimator.

An imaging system provided with a collimator as described previously may be implemented to perform a navigation and to know the position and/or the trajectory of a moveable element. "Element" is here taken to mean not just a part of the anatomy of a patient but also an object or a tool that is displaced with respect to the X-ray source.

In the case where it is wished to carry out a navigation of a tool the X-ray sensor or sensors used to detect the X-ray planes coming from the slots of the collimator are arranged directly on the tool.

Figure 9:
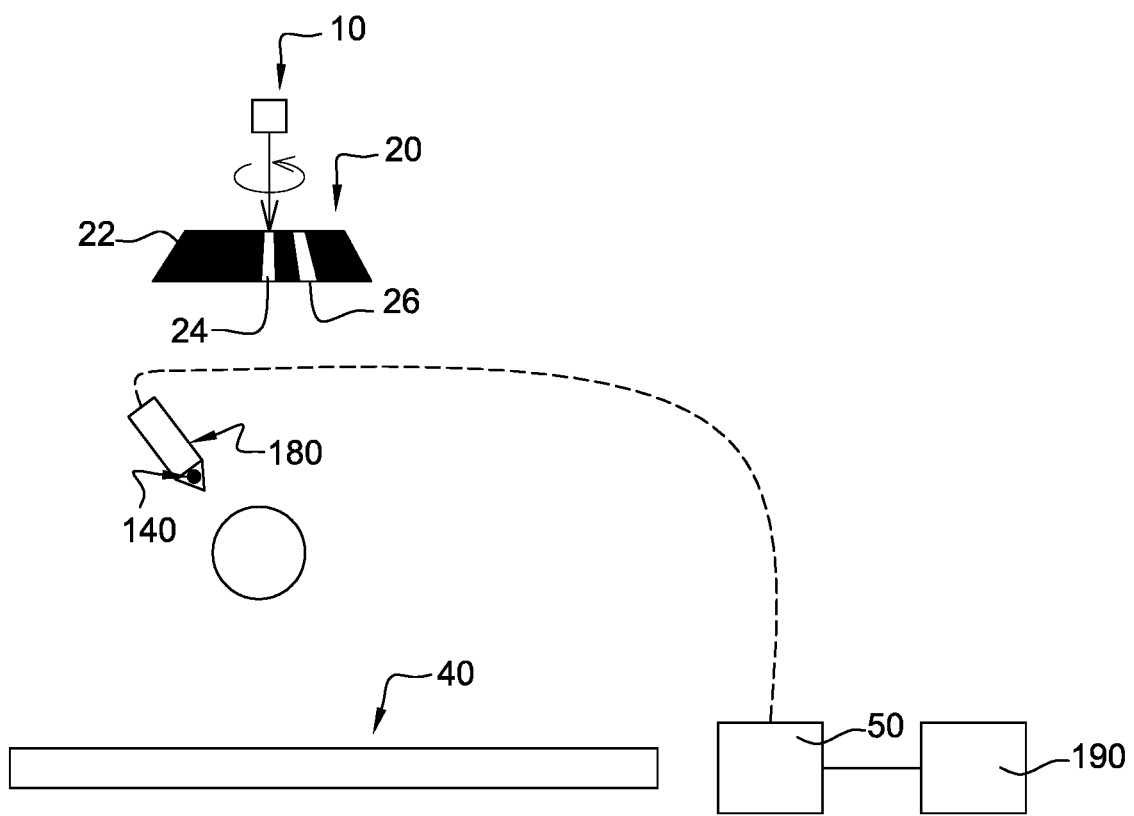
FIG. 9 illustrates an X-ray imaging system with rotary collimator making it possible to follow the navigation of an object provided with at least one X-ray sensor.

In FIG. 9, the object of which it is wished to follow the trajectory and the position with respect to a given coordinate system is for example a surgical instrument 180 provided with an X-ray sensor 140 fixed near to or on the tip of the instrument 180 and intended to be displaced between the X-ray source 10 and the X-ray detector 40 in the form of imager. The X-ray sensor 140 is coupled to a processing unit 50 as mentioned previously.

The rotating collimator 20 is in this case used to make it possible to determine the position of the instrument 180 and to follow its trajectory.

The distance between the X-ray source 10 and the X-ray imager 40 is this time known and fixed, and the position of the sensor 140 fixed on the instrument 180 is determined for example in the same way as in the exemplary embodiment described previously for determining the position of a sensor of the imager.

The sensor 140 on the instrument 180 makes it possible to detect an intersecting straight line between a first X-ray plane coming from the first slot of the collimator 20 and a second X-ray plane coming from the second slot of the collimator 20.

From this straight line is deduced a projection of the sensor 140 in the plane of the imager, this projection corresponding to an intersection of the intersecting straight line with the plane of the imager.

It is next possible to follow the displacement of the instrument 180 by following the displacement of this projection in the plane of the imager 40. A radiographic image display device 190 making it possible to follow in real time said displacement may be provided. A digital model of the object 180 is created for this purpose, then displayed on the display device 190. The digital model is then animated in an image as a function of the displacement made by the object 180.

Such a navigation principle applies to the monitoring of surgical operations in real time, but also to certain examinations or for the precise positioning of patients with respect to an X-ray imaging apparatus.

Figure 10:
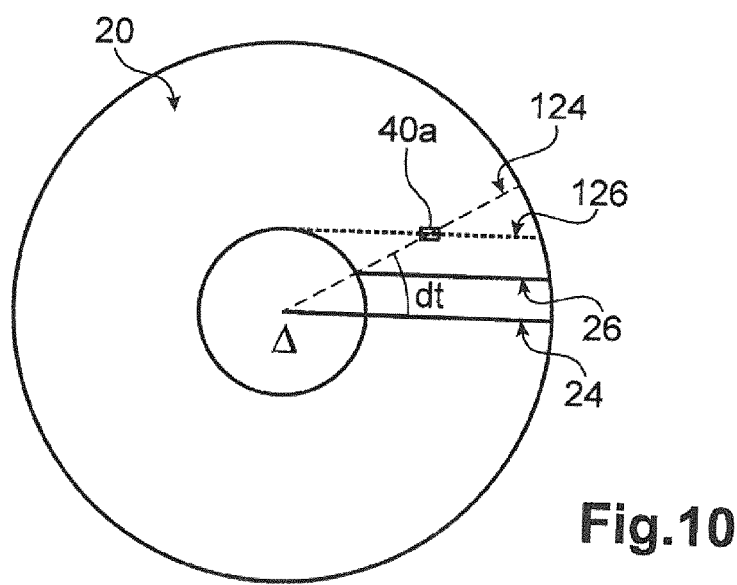
FIG. 10 illustrates an alternative layout of the rotary collimator.

An alternative layout of the rotary collimator is illustrated in FIG. 10, in which the two slots 24, 26 of the collimator are represented according to a position of the collimator taken at a first instant $t_0$.

Here again, the slots 24, 26 are laid out in such a way that the first slot 24 extends in a first direction $d_1$ which is secant to the axis of rotation Δ of the support 20 whereas the second slot 26 extends for its part in a second direction $d_2$ which does not go through the axis of rotation Δ of the support 20. The layout of the collimator differs from that given previously in relation with FIG. 1, in that the directions $d_1$ and $d_2$ of the slots 24, 26 are this time parallel.

An X-ray sensor 40a is capable of detecting an X-ray plane 126 coming from the second slot 26 when it is located in a given position at the first instant $t_0$, and of detecting another X-ray plane 126 coming from the first slot 24 when it is located in a position corresponding to a later instant $t_0+dt$, the intersection between these two planes 124, 126 providing information on the position of the sensor 40a.

The invention claimed is:

1. An X-ray imaging device comprising:
   a collimator formed of a support, the support being configured to rotationally move around itself and with respect to an axis of rotation passing through a main plane of the support, the support comprising:
   a region which is opaque to X-rays, and
   at least one first slot and at least one second slot passing through said opaque region, the at least one first slot and the at least one second slot being transparent to X-rays, the at least one first slot and the at least one second slot each extending in a given plane parallel to the main plane of the support and respectively in a first direction passing through the axis of rotation and in a second direction which is not secant to the axis of rotation,
   wherein the first direction and the second direction form between them a non-zero angle, such that, when an X-ray source is positioned behind said collimator to provide X-rays, at least two X-ray planes are generated from the at least one first slot and the at least one second slot.

2. The X-ray imaging device according to claim 1, wherein the at least one first slot and the at least one second slot have different widths.

3. The X-ray imaging device according to claim 1, wherein the support further comprises a region which is transparent to X-rays and situated in the given plane and juxtaposed with the opaque region.

4. The X-ray imaging device according to claim 1, wherein the support is a plate in the form of disc or portion of disc.

5. An X-ray imaging system comprising:
   an X-ray source,
   a device configured to determine the position of at least one element with respect to a given coordinate system, the element being provided with one or more X-ray sensors, the device comprising:
   an X-ray imaging device according to claim 1,
   a processor configured to determine at least one intersecting straight line between a first X-ray beam and a second X-ray beam detected by a same X-ray sensor among said sensors, the first beam coming from the X-ray source and having passed through the at least one first slot and the second X-ray beam coming from the X-ray source and having passed through the at least one second slot.

6. The X-ray imaging system according to claim 5, further comprising:
an imager,
wherein the support of the collimator is provided with a region which is radio-transparent to X-rays juxtaposed with a radio-opaque region, the system being laid out in such a way that, during a rotation of the collimator around itself, the source is during one phase exposed to the imager through the transparent region then during another phase masked from this imager by the opaque region and exposed solely through the at least one first slot and the at least one second slot,
wherein the processor is synchronised with the rotation of the collimator such that:
during said phase the processor is configured to trigger the acquisition of at least one radiographic image by the imager, and
during said other phase the processor is configured to estimate the position of said element.

7. The X-ray imaging system according to claim 5, wherein said element is an imager and wherein said X-ray sensors are pixels of the imager or are arranged on a matrix of pixels of the imager.

8. The X-ray imaging system according to claim 5, the device being configured to determine the position of the element with respect to the source.

9. The X-ray imaging system according to claim 5, wherein the element is an object that can be displaced with respect to the X-ray source to which the X-ray sensor or sensors is or are attached.

10. The X-ray imaging system according to claim 9, the system further comprising:
an imager configured to produce a radiographic image; and
a display device configured to display a radiographic image produced by the imager and taking into account the displacement of the object.

11. The X-ray imaging system according to claim 9, wherein the element is a surgical tool.

12. The X-ray imaging system according to claim 5, wherein the source and the element are connected by a C-arm.

13. The X-ray imaging system according to claim 5, wherein the collimator is configured to be displaced with respect to the source outside of its axis of rotation.

14. A method for calibrating an X-ray imaging system according to claim 5, wherein said element is an imager provided with at least four X-ray sensors, comprising: the determination of the position of the imager with respect to the source or with respect to a reference coordinate system linked to a room in which the imaging system is located, the determination of the position of the imager including an estimation by a processing unit coupled to the imager of at least four distinct straight lines each linking the source and a sensor among said at least four sensors of the imager.

* * * * *

UNITED STATES PATENT AND TRADEMARK OFFICE
CERTIFICATE OF CORRECTION

| | |
|---|---|
| PATENT NO. | : 10,729,390 B2 |
| APPLICATION NO. | : 15/770954 |
| DATED | : August 4, 2020 |
| INVENTOR(S) | : Yannick Grondin et al. |

Page 1 of 1

It is certified that error appears in the above-identified patent and that said Letters Patent is hereby corrected as shown below:

On the Title Page

(71) Applicants: "SURGIQUAL INSTITUTE, La Tronche (FR)" should read -- SURGIQUAL INSTITUTE, Meylan (FR) --

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*